(12) United States Patent
Eaton

(10) Patent No.: US 6,520,989 B1
(45) Date of Patent: Feb. 18, 2003

(54) EXTREME VOLUME FLEXIBLE INTEGRITY PROSTHESIS

(75) Inventor: L. Daniel Eaton, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 0 days.

(21) Appl. No.: 09/484,155

(22) Filed: Jan. 18, 2000

(51) Int. Cl.[7] .............................. A61F 2/52; A61F 2/14
(52) U.S. Cl. ............................................ 623/7; 623/4.1
(58) Field of Search ................................. 623/8, 7, 4.1

(56) References Cited

U.S. PATENT DOCUMENTS

| | | |
|---|---|---|
| 2,580,264 A | 12/1951 | Wright et al. |
| 3,366,975 A | 2/1968 | Pangman |
| 3,710,800 A | 1/1973 | Carey |
| 3,811,133 A | 5/1974 | Harris |
| 3,845,507 A | 11/1974 | Kirby et al. |
| 3,897,376 A | 7/1975 | Lampe |
| 3,905,376 A | 9/1975 | Johnson et al. |
| 3,925,277 A | 12/1975 | Lampe |
| 4,024,876 A | 5/1977 | Penrock |
| 4,086,666 A | 5/1978 | Vaskys et al. |
| 4,185,332 A | 1/1980 | Jahnig |
| 4,222,387 A | 9/1980 | Tetu |
| 4,245,644 A | 1/1981 | Evans |
| 4,253,201 A | 3/1981 | Ross et al. |
| 4,263,682 A | 4/1981 | Bejarno |
| 4,364,880 A | 12/1982 | Howse |
| 4,369,792 A | 1/1983 | Miller |
| 4,401,492 A | 8/1983 | Pfrommer |
| 4,546,899 A | 10/1985 | Williams |
| 4,549,529 A | 10/1985 | White |
| 4,574,780 A | 3/1986 | Manders |
| 4,600,551 A | 7/1986 | Erb |
| 4,637,398 A | 1/1987 | Sherwood |
| 4,661,187 A | 4/1987 | Beasley |
| 4,668,567 A | 5/1987 | Williams |
| 4,671,255 A | 6/1987 | Dubrul et al. |

(List continued on next page.)

FOREIGN PATENT DOCUMENTS

| | | |
|---|---|---|
| DE | 4115428 | 11/1992 |
| EP | 392960 | 10/1990 |
| GB | 2202745 | 10/1988 |

OTHER PUBLICATIONS

Callingham, K.; *An Anatomical Retention Technique for Orbital Facial Prosthesis:* The University of Texas Health Science Center at Dallas, Dallas, Texas, 1984.

Primary Examiner—Bruce Snow
Assistant Examiner—Brian E. Pellegrino
(74) Attorney, Agent, or Firm—Ray F. Cox, Jr.

(57) ABSTRACT

A flexible external prosthesis formed by first creating a thin walled hollow elastomeric shell of the shape required for anatomical augmentation. The interior of the hollow shell is filled with a flexible foam body formed into the same shape. The foam is formed by either of two methods. In one method the same mold used to form the thin walled hollow shell is used again to shape the foam into the same shape as the hollow shell. The hollow prosthesis may then be opened, the foam body inserted and the shell resealed. In another method, the foam is injected into the hollow shell while it is contained in the mold. The foam is desirably a two-part material which chemically generates a foaming agent when the two parts are mixed together. The foam then expands into the interior of the hollow shell and assumes the shape imposed by the mold. The foam body is lubricated to ensure free movement of the shell with respect to the foam body, desirably using a triglyceride oil, such as soy bean oil. By using the foam body to support the hollow prosthesis shell, it is possible to make the thickness of the shell walls thinner and thus more natural in feel and appearance. The foam body is colored with an opaque pigment and the shell is colored with a translucent pigment.

9 Claims, 7 Drawing Sheets

U.S. PATENT DOCUMENTS

| | | |
|---|---|---|
| 4,676,795 A | 6/1987 | Grundei |
| 4,681,587 A | 7/1987 | Eberl et al. |
| 4,685,447 A | 8/1987 | Iversen et al. |
| 4,699,144 A | 10/1987 | Sherwood |
| 4,731,081 A | 3/1988 | Tiffany et al. |
| 4,735,754 A | 4/1988 | Buckner |
| 4,826,501 A | 5/1989 | Grundei |
| 4,841,992 A | 6/1989 | Sasaki et al. |
| 4,863,477 A | 9/1989 | Monson |
| 4,899,764 A | 2/1990 | Gauger et al. |
| 4,995,882 A | 2/1991 | Destouet et al. |
| 5,005,591 A | 4/1991 | Austad |
| 5,035,249 A | 7/1991 | Sasaki et al. |
| 5,035,758 A | 7/1991 | Degler et al. |
| 5,066,302 A | 11/1991 | Rice |
| 5,071,433 A | 12/1991 | Naestoft et al. |
| 5,091,121 A | 2/1992 | Nakada et al. |
| 5,098,330 A | 3/1992 | Greenberg |
| 5,116,370 A | 5/1992 | Foglietti |
| 5,133,752 A | 7/1992 | Mandelkern |
| 5,133,753 A | 7/1992 | Bark et al. |
| 5,282,856 A | 2/1994 | Ledergerber |
| 5,308,420 A | 5/1994 | Yang |
| 5,352,307 A | 10/1994 | Wild |
| 5,358,521 A | 10/1994 | Shane |
| 5,376,323 A | 12/1994 | Eaton |
| 5,496,367 A | 3/1996 | Fisher |
| 5,496,370 A | 3/1996 | Hamas |
| 5,522,892 A | 6/1996 | Lin |
| 5,527,359 A | 6/1996 | Nakamura et al. |
| 5,531,786 A | 7/1996 | Perry et al. |
| 5,607,473 A | 3/1997 | Weber-Unger et al. |
| 5,632,777 A | 5/1997 | Petrick |
| 5,645,597 A | 7/1997 | Krapiva |
| 5,658,329 A | 8/1997 | Purkait |
| 5,658,330 A | 8/1997 | Carlisle et al. |
| 5,700,288 A | 12/1997 | Eaton |
| 5,702,454 A | 12/1997 | Baumgartner |
| 5,824,075 A | 10/1998 | Thielbar |
| 5,855,606 A | 1/1999 | Eaton |
| 6,004,914 A | 12/1999 | Perella et al. | ns # EXTREME VOLUME FLEXIBLE INTEGRITY PROSTHESIS

BACKGROUND OF THE INVENTION

The present invention relates to an external prosthesis for augmenting deficient anatomy, and in particular, to an external prosthesis which has both visual and tactile similarities to the natural anatomy.

Prostheses, both internal and external, are known for the purpose of augmenting deficient anatomy. Both internal and external prostheses must accurately replicate the size and shape of the deficient anatomy and if possible, the function of the replicated anatomy. External prostheses present additional unique problems in that external prostheses, since they are not implanted within the body, are more exposed to the visual and tactile impressions of the person fitted with the prosthesis, and, in some cases, to other persons as well.

An example of an internal prosthesis is Carlisle et al. (U.S. Pat. No. 5,658,330) which discloses a breast prosthesis implant with an outer elastic shell which encloses a biocompatible fluid and a silicone foam insert having the shape and consistency of breast tissue. A possible material for the outer shell is silicone. In one embodiment the foam body has a volume substantially equal to the unstretched volume of the elastic shell. The outer elastic shell may be formed on a mandrel which may also be used as the form for a mold to shape the foam insert. Among the biocompatible fluids, saline and silicone gel are disclosed. Carlisle et al. note that the prior art discloses multilumen prostheses where a lubricating material is provided between an outer shell and an inner lumen. It is also disclosed that the silicone foam body formed as described in the patent comprises both open cell and closed cell characteristics. The foam body may be either bonded to a portion of the inner surface of the shell or left free floating. The method of manufacturing the silicone foam body requires the uncured silicone to be blended with air, injected into a mold, and placed under a vacuum while the mold is heated to cure the silicone.

The outer shell of Carlisle et al. is an elastic silicone. It is disclosed that the outer shell may be formed by repeated dipping of a breast shaped mandrel in a silicone dispersion. External breast prostheses are also known having elastic hollow shells of silicone rubber molded to the shape of a breast. Examples are disclosed in Eberl et al. (U.S. Pat. No. 4,681,587), Grundei (U.S. Pat. No. 4,676,795), and Eaton (U.S. Pat. No. 5,700,288).

Internal prostheses having internal foamed bodies are known. Carlisle et al. disclose a foam body made of foamed silicone. However, polyurethane foam bodies for breast prosthesis implants are also known; e.g., Pangman (U.S. Pat. No. 3,366,975) and Ledergerber (U.S. Pat. No. 5,282,856). Greenberg (U.S. Pat. No. 5,098,330) discloses a latex foam external breast prosthesis. Eberl et al. (U.S. Pat. No. 4,681,587) disclose an external breast prosthesis member formed from silicone in the shape of a breast with a cavity on the back side. The cavity is filed with a polyurethane foam member to prevent the silicone member from collapsing. Grundei discloses an external breast prosthesis consisting of an elastic silicone shell filled partly with a plastic or rubber sponge, such as polyurethane, and partly with a slowly flowing gel-like mass.

Various filling materials are known for prostheses. Carlisle et al. disclose filing a breast prosthesis with a biocompatible fluid, such as saline or silicone gel. For the purpose of making a breast prosthesis radiolucent, the prior art teaches the use of natural triglyceride oils as filling materials in breast prostheses. In particular, Destouet et al. (U.S. Pat. No. 4,995,882) disclose biocompatible triglycerides in breast implants and suggest peanut oil and sunflower seed oil as being suitable for this purpose. Destouet et al. do not disclose using the triglyceride oil as a lubricant between the silicone shell and the foam body, but the prior art does teach the desirability of lubricants in multilumen breast implants, e.g., Shane (U.S. Pat. No. 5,358,521), and Tiffany et al. (U.S. Pat. No. 4,731,081).

Various methods are known for forming prostheses. Carlisle et al. disclose molding a foam body separately from a shell, opening the shell, inserting the foam body into the shell and resealing the shell. A similar process is disclosed in Degler et al. (U.S. Pat. No. 5,035,758) where a synthetic resin composition is cured between two thermoplastic films in a mold.

Pfrommer (U.S. Pat. No. 4,401,492) discloses a method of forming a breast prosthesis in which a mandrel shaped like a natural breast is dipped into a silicone dispersion to form the forward wall of the breast prosthesis. A rear wall is secured to the front wall and a colorant is applied to the surface. The prosthesis is then dipped into a clear silicone dispersion to form a second skin. The second skin protects the colorant on the prosthesis. A gel fill is injected into the interior space.

Ledergerber (U.S. Pat. No. 5,282,856) discloses implants which contain compressive structures designed to disorganize the formation of scar tissue.

The limitations of the prior art are overcome by the present invention as described below.

SUMMARY OF THE INVENTION

The present invention is a flexible external prosthesis which may be used to augment deficient anatomy, as for example, replacing a breast removed by mastectomy or an eye prosthesis following removal of the eye or surrounding tissue.

The prosthesis is formed by first creating a thin walled hollow shell using, e.g., the technique described in U.S. Pat. No. 5,376,323. This technique uses room temperature vulcanizable silicone to form a thin wall inside a mold adapted to reproduce precisely the shape required for anatomical augmentation. Once the thin hollow shell has been formed, the interior is filled with a flexible foam, desirably polyurethane or latex foam. The foam is formed by either of two methods. In one method the same mold used to form the thin walled hollow shell is used again to shape the foam into the identical configuration. The hollow prosthesis may then be opened and the foam body inserted and the shell resealed.

In another method, the foam is injected into the hollow shell while it is contained in the mold. The foam is desirably a two-part material which chemically generates a foaming agent when the two parts are mixed together. The foam then expands into the interior of the hollow shell and assumes the shape imposed by the mold. Multiple vents may be required to provide exit ports for the gas generated in the process.

Using either method of preparing the foam body, the foam body may not naturally attach itself to the interior surface of the silicone shell. In certain applications such as breast prostheses, however, it may be desirable that the foam body be attached to the shell at the rear wall of the shell. Movement of at least the front wall of the shell with respect to the foam body is desirable for a natural feel and appearance.

The foam body may be of either an open cell or closed cell type. To ensure free movement of the shell with respect to the foam body, the foam is lubricated, desirably using a triglyceride oil, such as soy bean oil. In the case of an open cell foam, the triglyceride oil is impregnated into the foam body. In the case of a closed cell foam, the triglyceride resides on the surface of the foam body.

By using the foam body to support the hollow prosthesis shell, it is possible to make the shell walls thinner and thus more natural in feel and appearance. It is desirable that the shell thickness be in the range of 1.0 to 2.0 mm, although in certain applications the shell thickness may be as little as 0.04 mm and may be varied over the shell for the most desirable mechanical properties.

An external prosthesis made according to this invention is intended to replicate as nearly as possible the natural feel and appearance of the anatomical feature being replicated. Accordingly, it is desirable that the foam body be colored with an opaque pigment and that the shell be colored with a translucent pigment. The combination provides a more natural replication of the appearance of human skin over underlying tissue. Additional enhancements of the natural appearance can be obtained by adding colorants to the lubricating oil; e.g., to mimic the appearance of blood below the surface of the skin. Thin hollow tubes affixed to the inner surface of the shell may mimic blood vessels and in conjunction with the appropriately colored lubricating oil provide a high degree of realistic simulation of the appearance of natural skin and the underlying tissue.

Further to enhance the natural tactile characteristics of the prosthesis, the foam body may desirably be formed at least in part with "accordioned" sections; i.e., sections with wedges removed so as to allow for greater resilience of portions of the foam body. The triglyceride lubrication combines with the accordioned sections to allow selected portions of the prosthesis to be compressed in a more natural manner. This technique is most likely to be applicable to external breast prostheses. In a breast prosthesis, it is desirable for a natural response that the inferior portion of the prosthesis be more compressible than the superior portion. The provision of a translucent pigment on the shell acts to hide the removed wedges of foam body and prevents the loss of the illusion of a natural appearance.

It is preferable that the prosthesis be provided with a valve for the injection of filling material. It is desirable to adjust the pressure of the filling material to achieve the optimum naturalistic resilience of the elastomer shell.

The present invention is an extremely lightweight flexible prosthesis with a thin outer shell of elastomer, such as silicone rubber, and an inner foam body, both having an elastic memory with predictable shape. The inner foam body provides resilience and support for the thin walls of the elastomeric shell. The foam body is saturated with a natural oil, such as a triglyceride oil including soybean oil, for lubrication for independent flexibility and movement between the outer shell and the inner foam body. The device provides a shape that is soft, forgiving and especially light in weight, yet maintains its original formed shape.

Since the outer shell seals the interior from contact with the atmosphere, the environment of the interior including the foam body is oxygen free. This can be important when a natural oil is used for lubrication of the foam body, since natural oils such as soybean oil oxidize and deteriorate in the presence of oxygen. Furthermore, many foamed elastomers can deteriorate when exposed to air. The inner foam body prevents the walls of the outer shell from collapse, rippling, crimping and creasing. Also the support provided by the inner foam body allows the walls of the shell to be made thinner for more flexibility and natural feel. Thin elastomer walls are also subject to tearing which is alleviated by the support provided by the foam body.

A prosthetic device made according to the present invention may be employed for alloplastic restoration, reconstruction of ablative facial, head and neck disease or trauma, mastectomies, and amputations. The device is however preferably limited to external prosthetic applications and is not implantable.

It is therefore an object of the present invention to provide for an external prosthesis which has properties that provide both visual and tactile similarities to natural human anatomy.

This and other objects and advantages of the present invention will be apparent from a consideration of the following detailed description of the preferred embodiments in conjunction with the appended drawings as described following.

DETAILED DESCRIPTION OF THE PREFERRED EMBODIMENTS

The present invention is a flexible prosthesis which may be used to augment deficient anatomy, as for example replacing a breast removed by mastectomy or an eye prosthesis following removal of the eye or surrounding tissue.

Figure 1:
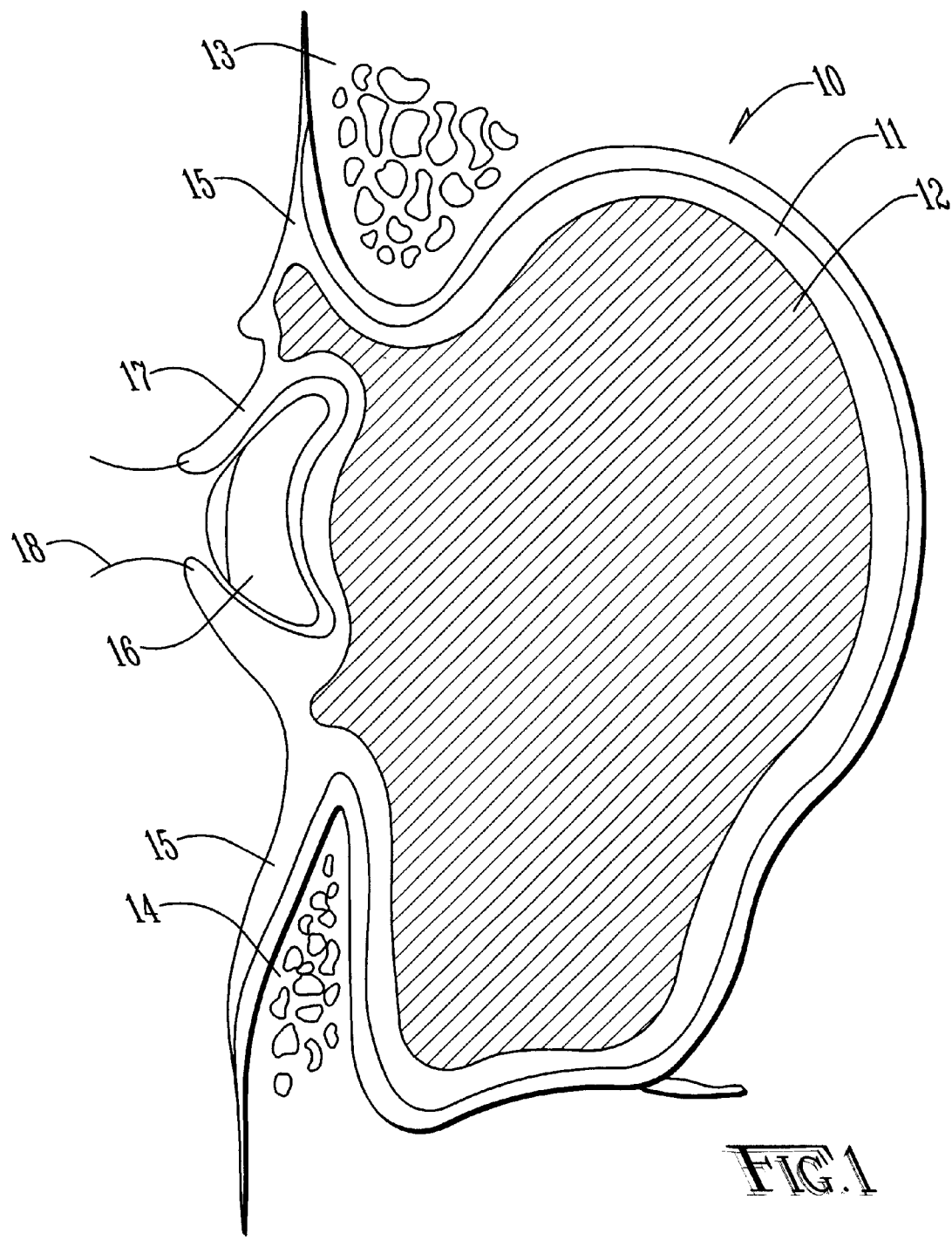
FIG. 1 is a left side elevational view in cross section of an eye prosthesis according to the present invention.
Figure 3:
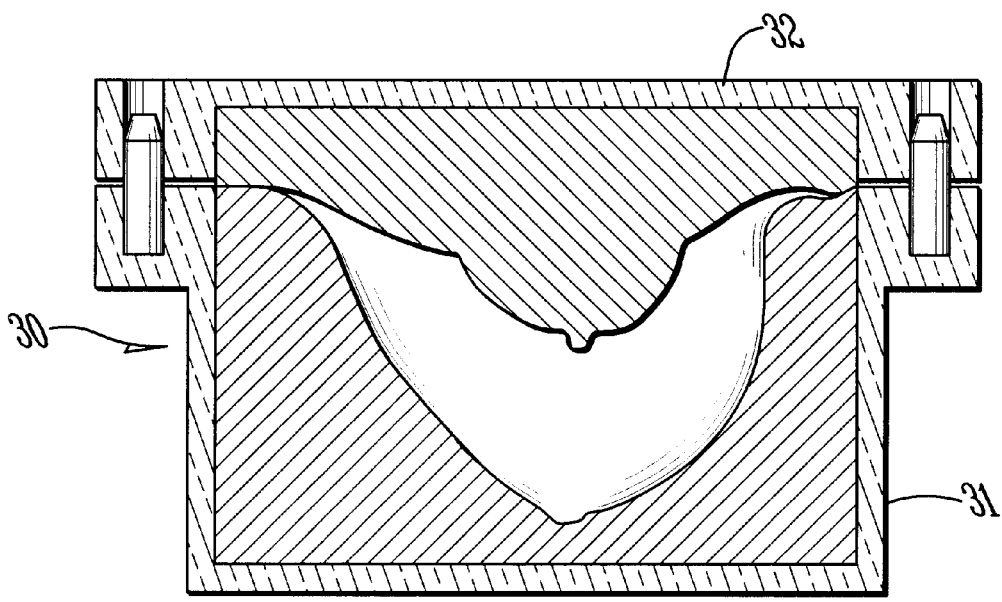
FIG. 3 is an elevational view of a mold for forming a breast prosthesis.

With reference to FIGS. 3–6, the prosthesis is formed by first creating a thin walled hollow shell, preferably made of an elastomer, such as silicone rubber. The shell may be made using the technique described in U.S. Pat. No. 5,376,323, which is incorporated herein by reference. This technique uses room temperature vulcanizable (RTV) silicone to form a thin wall inside a mold adapted to reproduce precisely the shape required for anatomical augmentation. FIG. 3 shows a cross section of a typical two-part mold 30 for forming a breast prosthesis. The lower part 31 of the mold 30 replicates the anterior shape of a breast, while the upper part 32 provides an arched or vaulted posterior for contact with the chest of the user. Although illustrated by a breast prosthesis, the present invention may be employed for other types of prostheses and is not limited to breast prostheses. An example of an eye prosthesis 10 is shown in FIG. 1 where an elastomeric shell 11 and included foam body 12 fill the cavity formed by the removal of an eye and surrounding tissue. The cavity is defined by the remaining bone of the orbit 13 and maxilla 14. The elastomeric shell 11 is formed with periphera 15 which blend into the natural skin. The external appearance of a natural eye 16, eyelids 17 and eyelashes 18 are duplicated as well using techniques known in the art.

Figure 4:
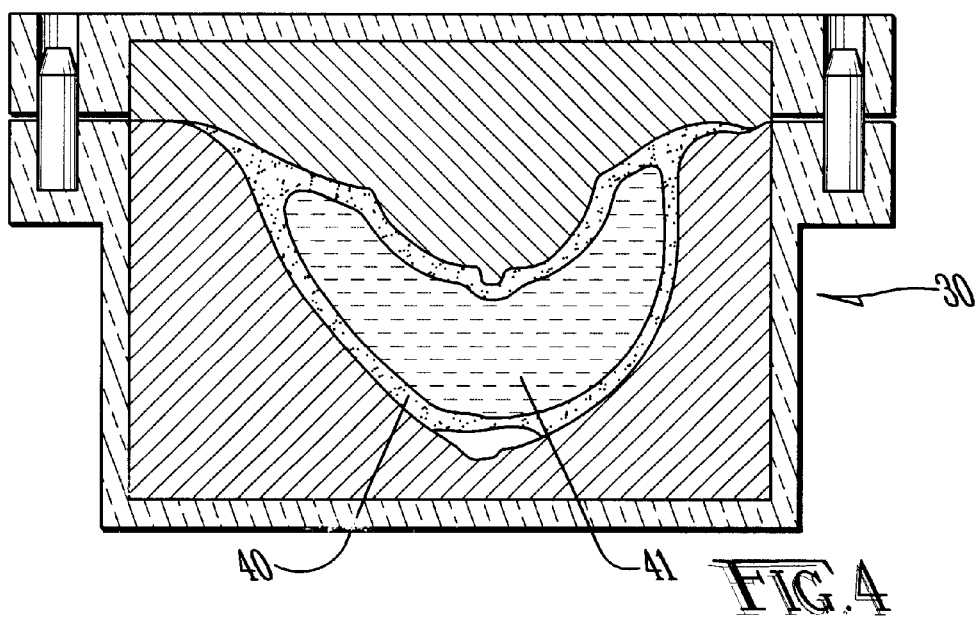
FIG. 4 is an elevational view of the mold of FIG. 3 injected with an elastomer that has cured to form a thin shell.

As shown in FIG. 4, the mold 30 is injected with RTV silicone which cures to form a thin walled shell 40 while the remaining unvulcanized RTV silicone 41 is expressed from the shell 40. Silastic® Medical Adhesive Silicone Type A, a product of Dow Corning, is an RTV silicone which cures by reacting with moisture in the air, liberating acetic acid. A shell 40 formed from Silastic® RTV silicone has exceptional elastic properties which allows the shell 40 to tend to return to its original form even after repeated deformations. By utilizing a material that provides shape memory in the elastomer shell 40, no underlying foam body is necessary for providing the proper shape, but an underlying foam body does provide support, enhances the integrity of the elastomeric shell 40 and allows thinner, more naturalistic appearing walls of the elastomeric shell 40.

Figure 6:
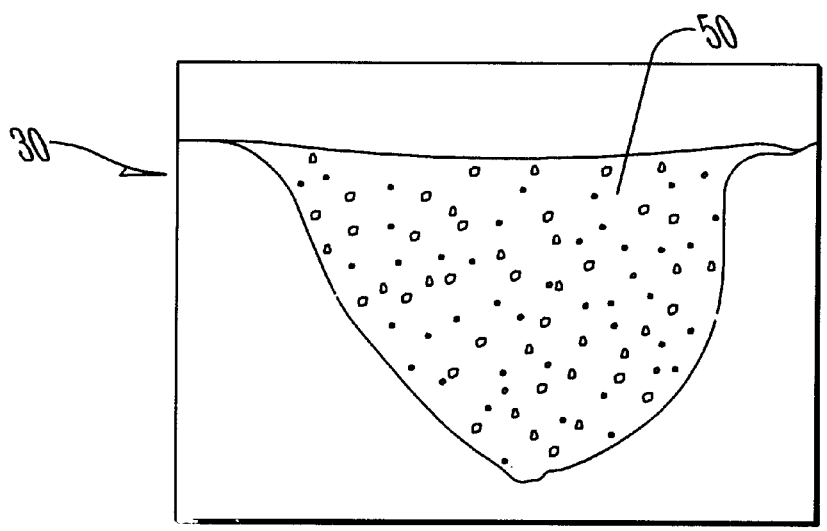
FIG. 6 is an elevational view of the mold of FIG. 3 injected with a foam generating material.

Once the thin hollow shell 40 has been formed, the interior is filled with a flexible elastomer foam body 50, desirably polyurethane or latex foam. The foam body 50 is formed by either of two methods. In one method the elastomeric shell 40 is removed from the mold 30 and the same mold 30 used to form the thin walled hollow elastomeric shell 40 is used again to shape the foam body 50 into the identical shape as shown in FIG. 6. Once the foam body 50 has cured, the elastomeric shell 40 may then be opened, the cured foam body 50 inserted and the shell 40 resealed.

Figure 5:
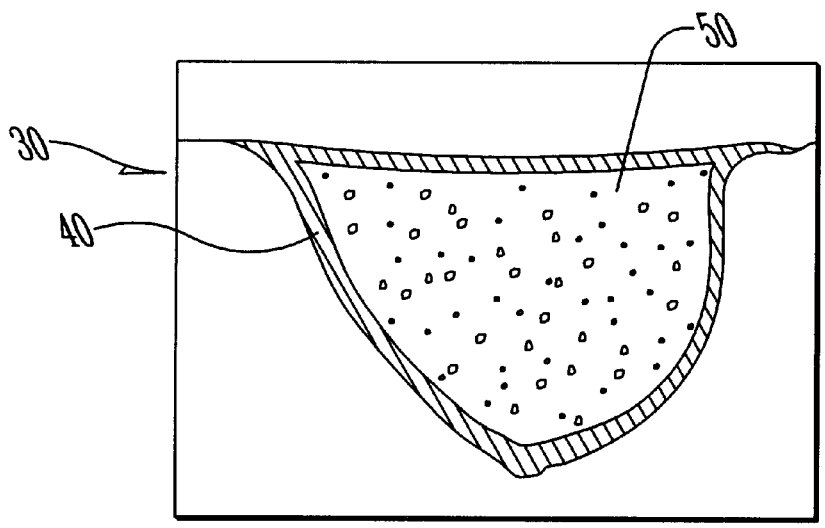
FIG. 5 is an elevational view of the mold of FIG. 4 injected with a foam generating composition to form a foam body within the elastomer shell.

In another method, foam forming material is injected into the hollow elastomeric shell 40 while it is contained in the mold 30 as shown in FIG. 5. The foam forming material used to form the foam body 50 is desirably a two-part material which chemically generates a foaming agent when the two parts are mixed together. Various examples of such two-part foaming materials as known in the art would be suitable for the practice of the present invention. The foam expands into the interior of the elastomeric shell 40 or into the mold 30 alone and in either case assumes the shape imposed by the mold 30. Multiple vents in the mold 30 may be required to provide exit ports for the gas generated in the process.

When molding the foam body 50, a separator is needed to allow the foam body 50 to be separated from the mold 30. The separator is applied to the surface of the mold before injection of the foam material from which the foam body 50 is formed. It is known in the prior art to use a water based latex enamel as the separator with a latex foam. The separator will then bond to the surface of the foam body 50 and produce a colored surface. This is desirable in many prosthetic applications.

In the preferred embodiment, no part of the foam body 50 is attached to the interior surface of the elastomeric shell 40.

Figure 2:
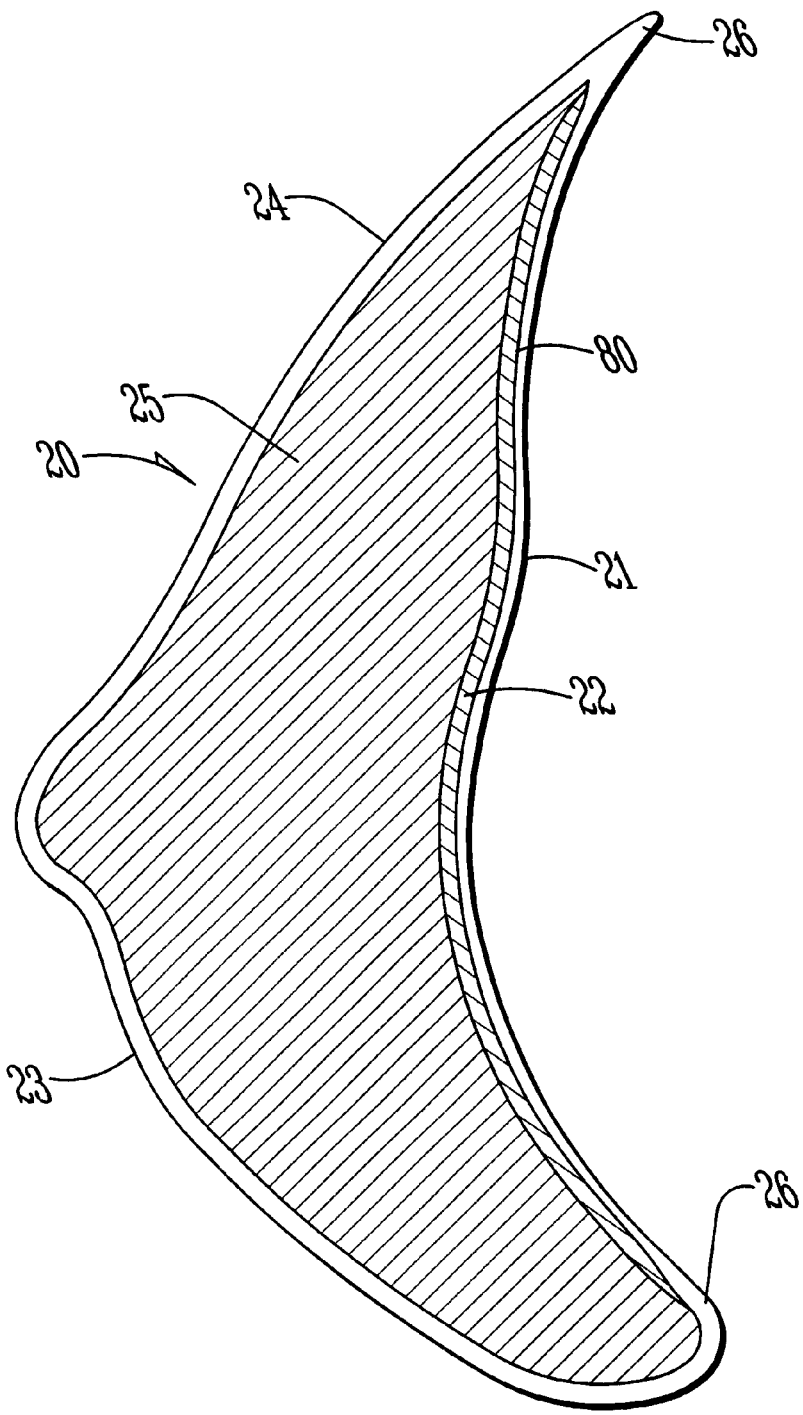
FIG. 2 is a left side elevational view in cross section of a breast prosthesis according to the present invention.

In certain applications, however, it may be desirable that the foam body 50 be attached to the shell 40 at some point. For example, in the case of a breast prosthesis 20 as shown in FIG. 2, it may be desirable that the posterior wall 21 of the shell 24 be attached to the posterior surface 22 of the foam body 24. Attachment can be accomplished by, e.g., the injection of RTV silicone 80 between the posterior wall 21 of the shell 24 and the posterior surface 22 of the foam body 25. Movement of at least the anterior wall 23 of the shell 24 with respect to the foam body 25 is desirable for a natural feel and appearance.

With reference to the generic description of the present invention in FIGS. 3–6, the foam body 50 may be of either an open cell or closed cell type. To ensure free movement of the shell 40 with respect to the foam body 50, the foam body 50 is lubricated, desirably using a natural triglyceride oil, such as soy bean oil. In the case of an open cell foam, the triglyceride oil is impregnated in the foam body 50. In the case of a closed cell foam, the triglyceride resides on the surface of the foam body 50 next to the interior surface of the shell 40. The use of a natural triglyceride as the filling material is desirable in the case of a leak as the natural triglyceride is less likely to be harmful to the user of the prosthesis. When an open cell foam is used, the triglyceride oil may be impregnated into the foam body 50 in an amount sufficient to adjust the weight of the prosthesis. For example, in the case of a breast prosthesis, it is desirable that the prosthesis be similar in weight to the remaining natural breast. An open cell foam is able to absorb more filling material which allows greater latitude in the adjustment of the weight of the prosthesis.

Figure 10A:
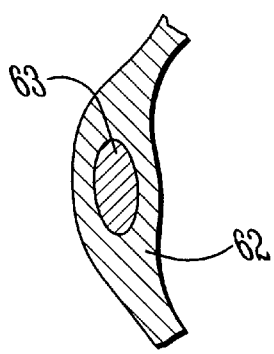
FIG. 10A is a partial elevational cross section of a self-sealing valve embedded in an elastomeric wall.
Figure 10:
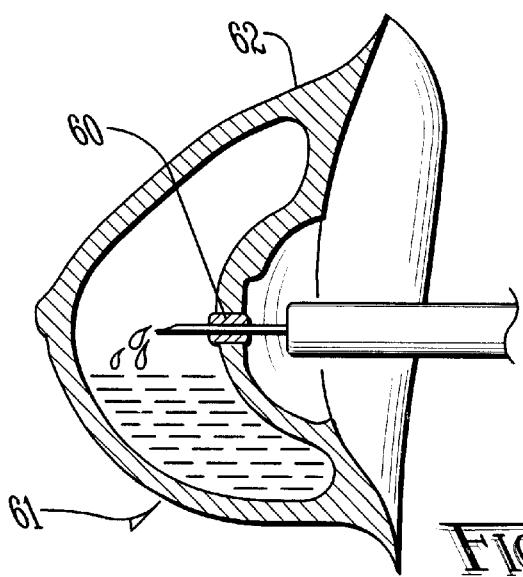
FIG. 10 is a left side elevational cross section of a breast prosthesis according to the present invention showing a self sealing valve on the posterior portion of the breast prosthesis.

With reference to FIG. 10, a valve 60 in the prosthesis 61 is provided for the injection of the triglyceride oil. The prosthesis 61 shown in FIG. 10 is a breast prosthesis for illustrative purposes; other types of prostheses may also be provided with a valve 60. In the illustration in FIG. 10, the foam body within the shell 62 is not shown for clarity of illustration. The valve 60 may also be used to inject other materials; e.g., other liquid or gaseous materials may be injected to adjust the weight or the pressure inside the elastomer shell 62 to obtain the optimum naturalistic feel and appearance. For example, in a breast prosthesis application, greater tension on the elastomeric shell 62 is desirable to avoid puckering and wrinkling when the prosthesis is worn within a bra. Variable inflation pressure alters the flexibility of the elastomeric shell 62 and also allows some alteration in the shape of the prosthesis. Such adjustments may be made as often as necessary during the lifetime of use of the prosthesis. The valve 60 is preferably a self-sealing type that may be used routinely to adjust the amount of filling material in the elastomeric shell. Self-sealing valves are known in the art. An example of a self-sealing valve 60 is shown in FIG. 10A wherein a latex plug 63 is encapsulated in the wall of the elastomeric shell 62. While a silicone rubber shell is not self-sealing, the latex plug 63 will seal itself after an injection needle has passed through it.

Referring again to FIGS. 3–6, it is desirable that the shell 40 be formed into the desired shape to augment a volume of deficient anatomy. Using an elastomer to form the shell 40 is desirable since the elastic properties of the elastomer have a "memory" and tend to return to the desired shape even after deformation. As the shell walls grow thinner however, the flexibility of the shell wall renders it more easily deformable and less likely to maintain the desired shape. Countering this consideration is the desirability of thin walls which are softer in texture, more flexible, and more nearly like natural bodily features, such as skin. By using the foam body 50 to support the hollow shell 40, it is possible to make the thickness of the shell walls thinner and thus more natural in feel and appearance. It is desirable that the shell wall thickness be in the range of 1.0 to 2.0 mm. Shell walls as thin as 0.04 mm may be desirable in some applications. It may also be desirable that the shell wall thickness be varied over the elastomeric shell 40 for optimal mechanical properties and tactile response.

With reference to FIG. 2, in the case of a breast prosthesis 20 made according to the present invention, it is desirable that the posterior wall 21 of the prosthesis 20 be vaulted so that only the lateral periphera 26 of the prosthesis 20 touches the skin of the user. The vaulting is desirable to avoid placing undue pressure on scar tissue that remains after a mastectomy.

Figure 11:
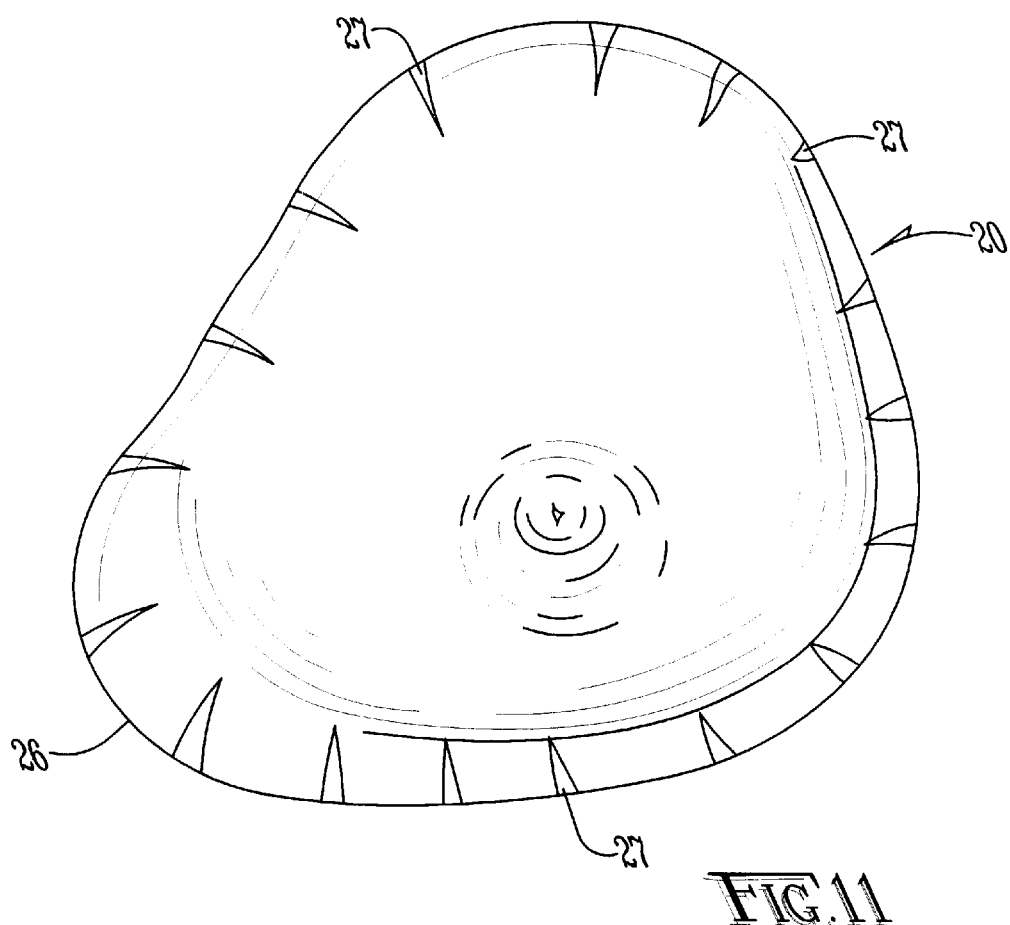
FIG. 11 is a front elevational view of a breast prosthesis according to the present invention showing venting slots on the lateral periphera of the breast prosthesis.

Vaulting is also desirable to avoid the buildup of moisture behind the prosthesis 20. Referring to FIG. 11, ventilation is also desirable and may be assisted by placing slotted vents 27 in the lateral periphera 26 of the prosthesis. This avoids blanching of skin, erythema or possible tissue necrosis.

Figure 7:
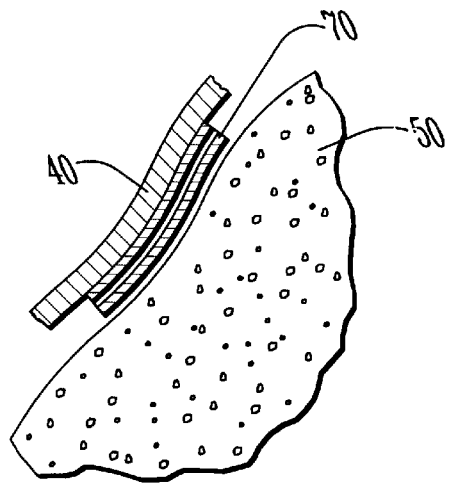
FIG. 7 is a partial elevational cross section of the breast prosthesis of FIG. 2 showing the additional of thin hollow tubes to the inner surface of the elastomer shell to simulate superficial a blood vessel.

An external prosthesis made according to this invention is intended to replicate as nearly as possible the natural feel and appearance of the anatomical feature being replicated. Accordingly, it is desirable that the foam body 40 be colored with an opaque pigment and that the shell 50 be colored with a translucent pigment. The combination provides a more natural replication of the appearance of human skin over underlying tissue. In addition, the triglyceride oil may be altered with a colorant. For example, the triglyceride oil may be colored using; e.g., methylene blue, to simulate the appearance of blood beneath the skin. Additionally as shown in FIG. 7, thin hollow tubes 70 may be affixed to the interior of the elastomer shell 40 to mimic the appearance of blood vessels below the skin. If the hollow tubes 70 are left open at each end they will naturally tend to fill with the colored triglyceride oil to give a depth of color to render the simulated blood vessel more noticeable. Further, the tubes 70 are desirably made of silicone elastomer and therefore collapsible as is true of natural blood vessels.

Figure 8:
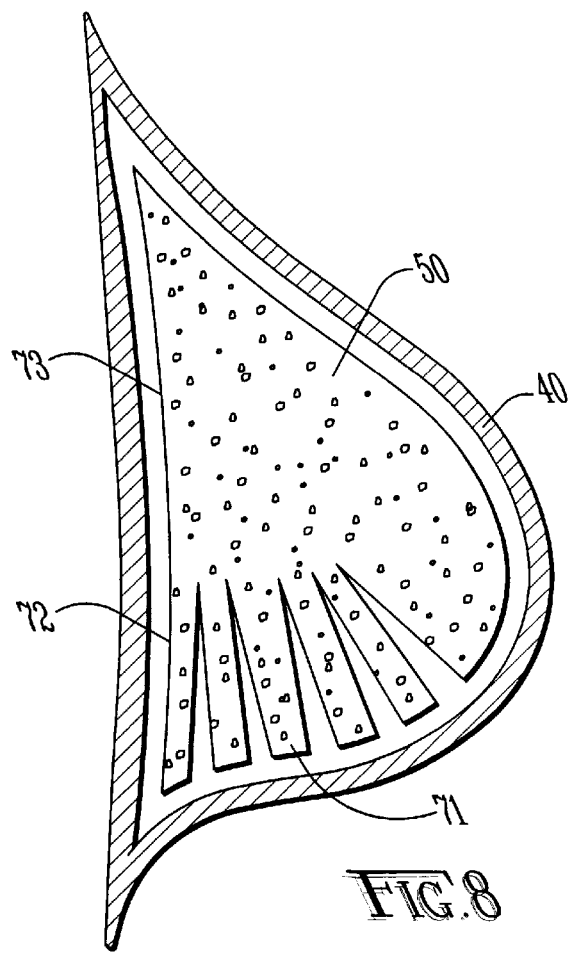
FIG. 8 is a right side elevational cross section of a breast prosthesis according to the present invention in which the inferior portion is "accordioned" to provide greater resilience.
Figure 9:
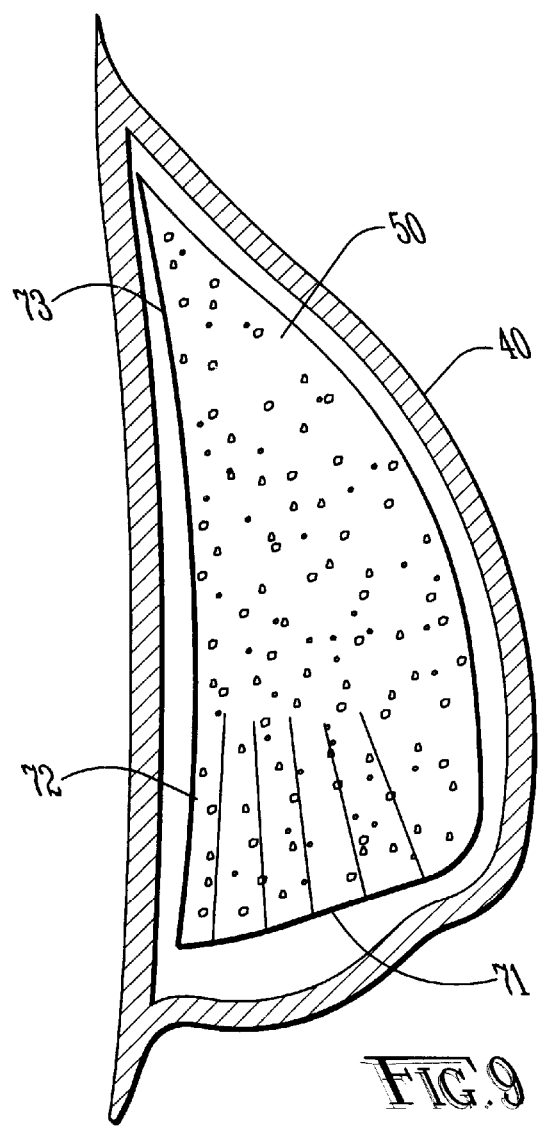
FIG. 9 is the breast prosthesis of FIG. 8 showing the effect of compressing the inferior "accordioned" portion.

Furthermore a shown in FIGS. 8 and 9, the foam body 50 may desirably be formed at least in part with "accordioned" sections 71; i.e., sections with wedges removed so as to allow for greater resilience of portions of the foam body 50. The triglyceride lubrication combines with the accordioned sections 71 to allow selected portions of the prosthesis to be compressed in a more natural manner. This technique is most likely to be applicable to external breast prostheses. The provision of a translucent pigment on the shell 40 acts to hide the removed wedges of foam body 50 and prevents the loss of the illusion of a natural appearance. In FIG. 8, a breast prosthesis is illustrated with "accordioned" sections 71 in the inferior portion 72 and not in the superior portion 73 of the prosthesis. Such an arrangement allows the inferior portion 72 to collapse with greater resilience that the superior portion 73, more nearly replicating the action of a natural breast when compressed.

The present invention has been described with reference to certain preferred and alternative embodiments that are intended to be exemplary only and not limiting to the full scope of the present invention as set forth in the appended claims.

What is claimed is:

1. An external prosthesis for augmenting deficient anatomy, comprising:

a fluid tight elastomeric shell formed in a desired shape to augment the deficient anatomy;

said elastomeric shell having walls with a thickness less than about 2.0 millimeters;

an elastomeric foam body formed into a shape allowing said foam body to fill said elastomeric shell and to support said walls of said elastomeric shell; and lubricating oil disposed within said shell for low friction movement of said walls of said elastomeric shell with respect to said foam body; wherein said elastomeric foam body further comprises opaque coloring means and said elastomeric shell further comprises translucent coloring means; and wherein said lubricating oil further comprises means for coloring said lubricating oil.

2. The external prosthesis of claim 1 wherein said foam body further comprises a posterior surface and means attaching said posterior surface of said foam body to said posterior wall of said elastomeric shell.

3. The external prosthesis of claim 1, wherein said anterior wall of said elastomeric shell has an interior surface having open-ended hollow tubes affixed to said interior surface.

4. An external prosthesis for augmenting deficient anatomy, comprising:

a fluid tight elastomeric shell formed in a desired shape to augment the deficient anatomy;

said elastomeric shell having walls with a thickness less than about 2.0 millimeters;

an elastomeric foam body formed into a shape allowing said foam body to fill said elastomeric shell and to support said walls of said elastomeric shell; and lubricating oil disposed within said shell for low friction movement of said walls of said elastomeric shell with respect to said foam body; wherein said elastomeric foam body further comprises opaque coloring means and said elastomeric shell further comprises translucent coloring means;

wherein said elastomeric shell comprises a posterior wall and an anterior wall replicating the appearance of a natural breast; and wherein said lubricating oil further comprises means for coloring said lubricating oil.

5. The external prosthesis of claim 4 wherein said elastomeric shell further comprises lateral periphera and said lateral periphera further comprises a plurality of vent slots for venting the anterior of said elastomeric shell.

6. An external prosthesis for augmenting deficient anatomy, comprising:

a fluid tight elastomeric shell formed in a desired shape to augment the deficient anatomy;

said elastomeric shell having walls with a thickness less than about 2.0 millimeters;

an elastomeric foam body formed into a shape allowing said foam body to fill said elastomeric shell and to support said walls of said elastomeric shell; and lubricating oil disposed within said shell for low friction movement of said walls of said elastomeric shell with respect to said foam body; wherein said elastomeric foam body further comprises opaque coloring means and said elastomeric shell further comprises translucent coloring means;

wherein said elastomeric shell comprises a posterior wall and an anterior wall replicating the appearance of a natural breast;

wherein said elastomeric foam body comprises a superior portion and an inferior portion and further wherein said inferior portion further comprises accordioning means for allowing said inferior portion to be more easily compressed than said superior portion; and wherein said accordioning means comprises one or more wedge-shaped cutouts in said inferior portion.

7. The external prosthesis of claim 6 wherein said lubricating oil comprises a triglyceride oil.

8. The external prosthesis of claim 7 wherein said triglyceride oil is soy bean oil.

9. The external prosthesis of claim 6 wherein said lubricating oil further comprises means for coloring said lubricating oil.

* * * * *